(12) United States Patent
Morii et al.

(10) Patent No.: US 9,994,530 B2
(45) Date of Patent: Jun. 12, 2018

(54) METHOD OF PRODUCING OPTICALLY ACTIVE 2-METHYLPIPERAZINE

(71) Applicant: Toray Fine Chemicals Co., Ltd., Tokyo (JP)

(72) Inventors: Seiji Morii, Tokai (JP); Takeshi Nishikawa, Tokai (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days. days.

(21) Appl. No.: 15/501,360

(22) PCT Filed: Aug. 3, 2015

(86) PCT No.: PCT/JP2015/071906
§ 371 (c)(1),
(2) Date: Feb. 2, 2017

(87) PCT Pub. No.: WO2016/021524
PCT Pub. Date: Feb. 11, 2016

(65) Prior Publication Data

US 2017/0226066 A1    Aug. 10, 2017

(30) Foreign Application Priority Data

Aug. 8, 2014   (JP) .................................. 2014-162138

(51) Int. Cl.
*C07D 241/04*     (2006.01)
(52) U.S. Cl.
CPC .................. *C07D 241/04* (2013.01)

(58) Field of Classification Search
None
See application file for complete search history.

(56) References Cited

FOREIGN PATENT DOCUMENTS

| JP | 4-360877 A | | 12/1992 |
|---|---|---|---|
| JP | 2002-332277 A | | 11/2002 |
| JP | 2003-286268 A | | 10/2003 |
| JP | 2003286268 A | * | 10/2003 |
| JP | 2004-161749 A | | 6/2004 |
| JP | 2004161749 A | * | 6/2004 |
| JP | 2005-120014 A | | 5/2005 |
| JP | 2005-120015 A | | 5/2005 |
| JP | 2005120014 A | * | 5/2005 |

OTHER PUBLICATIONS

Bergfors, Terese. Journal of Structural Biology 142 (2003) 66-76.*

* cited by examiner

*Primary Examiner* — Deepak R Rao
*Assistant Examiner* — Laura M Daniel
(74) *Attorney, Agent, or Firm* — DLA Piper LLP (US)

(57) ABSTRACT

A method of producing an optically active 2-methylpiperazine includes: adding a solvent to a solution of the optically active 2-methylpiperazine to carry out solvent replacement, and then being crystallized to obtain crystals of the optically active 2-methylpiperazine. The method allows the optically active 2-methylpiperazine to be purified during the crystallization process, and thus it is possible to obtain an optically active 2-methylpiperazine having a high quality.

2 Claims, 2 Drawing Sheets

METHOD OF PRODUCING OPTICALLY ACTIVE 2-METHYLPIPERAZINE

TECHNICAL FIELD

This disclosure relates to a method of producing an optically active 2-methylpiperazine. More specifically, the disclosure relates to a method of producing an optically active 2-methylpiperazine having a high purity, which method is capable of industrially producing a large amount of the optically active 2-methylpiperazine at a high yield.

BACKGROUND

As a method of producing an optically active 2-methylpiperazine, for example, a method is known in which (±)-2-methylpiperazine is optically resolved with an optically active tartaric acid; or a method in which (±)-2-methylpiperazine is optically resolved with an optically active 2-phenoxypropionic acid. Further, as a method of isolating an optically active 2-methylpiperazine from the salt of the optically active 2-methylpiperazine with an optical resolution agent, obtained by the optical resolution, a method is known in which the optically active 2-methylpiperazine is separated by distillation; or a method in which the optically active 2-methylpiperazine is isolated as a mineral acid salt. In addition, as a method of isolating an optically active 2-methylpiperazine from the mineral acid salt of the optically active 2-methylpiperazine, a method is known in which the mineral acid salt is reacted with an alkali metal alkoxide in a lower alcohol, and after filtering the resulting solution and concentrating the filtrate, the crystal is crystallized (See, JP 2004-161749 A and JP 2002-332277 A).

However, since the optically active 2-methylpiperazine obtained by distillation has a high melting point of from 91 to 93° C., the optically active 2-methylpiperazine obtained by those methods solidifies at room temperature. Therefore, when the thus obtained optically active 2-methylpiperazine is used, for example, when it is weighed, dissolved, transferred or the like, it is necessary to heat and dissolve the 2-methylpiperazine, making it difficult to handle.

The problems associated with the optically active 2-methylpiperazine isolated by distillation can be solved, by using a method in which, after collecting the optically active 2-methylpiperazine as a mineral acid salt, the mineral acid salt of the optically active 2-methylpiperazine is reacted with an alkali metal alkoxide, and then the liberated optically active 2-methylpiperazine is crystallized, to obtain the 2-methylpiperazine as crystals, because the resulting optically active 2-methylpiperazine can be handled as crystals. However, since that method includes a step of forming the mineral acid salt of the optically active 2-methylpiperazine, it results in a longer production process. Further, when the salt is decomposed with an alkali metal alkoxide in an alcohol solvent, an excess amount of alkali metal alkoxide and/or inorganic salt is/are dissolved and mixed into the solution of the liberated optically active 2-methylpiperazine. Accordingly, a step of removing impurities such as the excess amount of alkali metal alkoxide and/or inorganic salt is required, thereby complicating the operation.

As described above, no industrially applicable method has been known which is capable of producing an optically active 2-methylpiperazine having a good handleability and favorable properties. Accordingly, there has been a demand to find an industrially applicable method that produces an optically active 2-methylpiperazine having a good handleability and favorable properties.

It could therefore be helpful to provide a method capable of industrially producing an optically active 2-methylpiperazine having a good handleability and favorable properties, with a short production process.

SUMMARY

We thus provide a method of producing an optically active 2-methylpiperazine, the method comprising: adding a solvent to a solution of the optically active 2-methylpiperazine to carry out solvent replacement, and then obtaining crystals of the optically active 2-methylpiperazine by crystallization.

The method is an industrially advantageous method because the production cost can be reduced due to short production process.

The optically active 2-methylpiperazine obtained by the method of producing an optically active 2-methylpiperazine has a better handleability when it is weighed, dissolved, transferred or the like, as compared to the one obtained by distillation.

It is possible to industrially produce an optically active 2-methylpiperazine in the form of crystals, which can be easily handled when it is weighed, dissolved, transferred or the like. Further, since the method of producing an optically active 2-methylpiperazine allows the optically active 2-methylpiperazine to be purified during the crystallization process, an optically active 2-methylpiperazine having a high quality can be obtained.

The optically active 2-methylpiperazine produced by the method of producing an optically active 2-methylpiperazine is useful as a raw material for pharmaceuticals.

DETAILED DESCRIPTION

Figure 1:
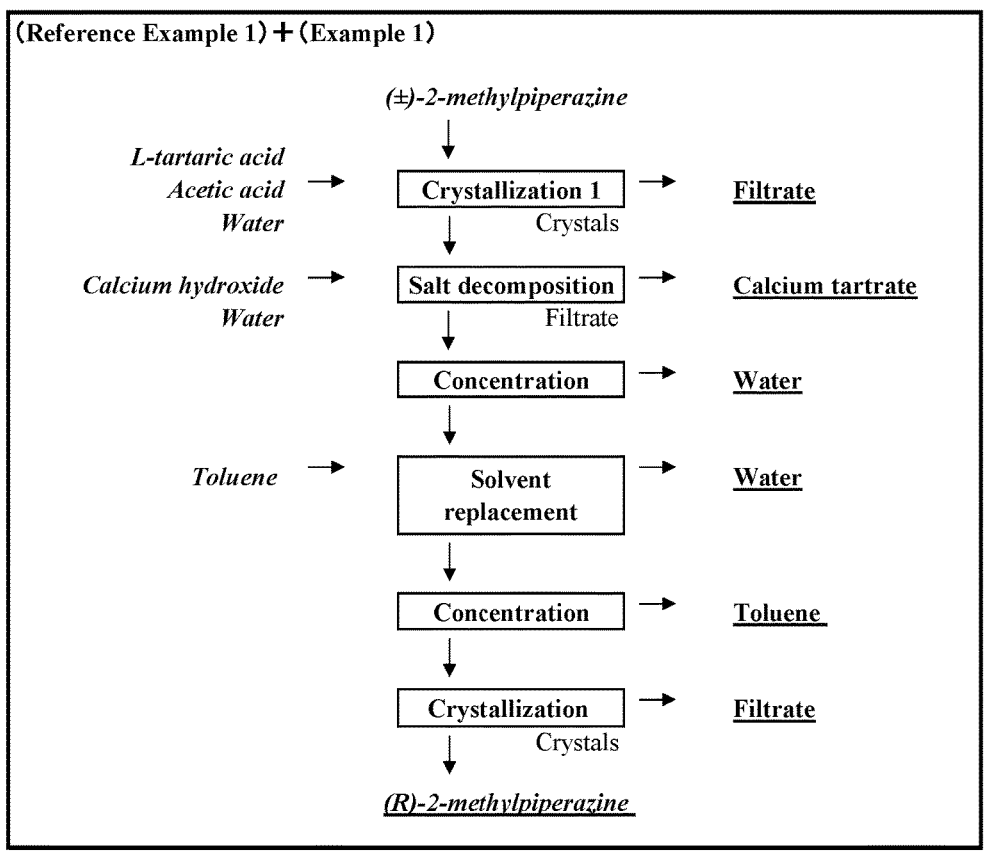
FIG. 1 is a process flow chart illustrating the steps carried out in Reference Example 1 through Example 1.

Our methods will now be described in detail.

Our method produces an optically active 2-methylpiperazine and comprises: adding a solvent to a solution of the optically active 2-methylpiperazine to carry out solvent replacement, and then obtaining crystals of the optically active 2-methylpiperazine by crystallization.

Examples of the solvent to be used in the solution of the optically active 2-methylpiperazine as a raw material include: aromatic hydrocarbons such as benzene, toluene, ethylbenzene, o-xylene, m-xylene, p-xylene, styrene, chlorobenzene, and naphthalene; aliphatic hydrocarbons such as pentane, hexane, heptane, octane, nonane, decane, and dodecane; halogen-containing solvents such as carbon tetrachloride, dichloromethane, chloroform, and 1,2-dichloroethane; alcohols such as methanol, ethanol, propanol, isopropanol, butanol, isobutanol, sec-butanol, tert-butanol, pentanol, 2-pentanol, hexanol, heptanol, and octanol; aliphatic esters such as allyl acetate, isobutyl acetate, isopropyl acetate, isopentyl acetate, ethyl acetate, vinyl acetate, phenyl acetate, butyl acetate, propyl acetate, benzyl acetate, methyl acetate, isobutyl formate, butyl formate, methyl propionate, ethyl propionate, methyl butyrate, ethyl butyrate, propyl butyrate, isopropyl butyrate, butyl butyrate, isobutyl butyrate, pentyl butyrate, isopentyl butyrate, ethyl isobutyrate, methyl isovalerate, and ethyl isovalerate; aromatic esters such as methyl benzoate, and ethyl benzoate; ethers such as tetrahydrofuran, cyclopentyl methyl ether, diethyl ether, diisopropyl ether, dibutyl ether, anisole, and diphenyl ether; ketones such as acetone, acetyl acetone, ethyl methyl ketone, cyclopentanone, cyclohexanone, 3-heptanone, 4-heptanone, 2-pentanone, and 3-pentanone; nitriles such as acetonitrile and the like. The solvent to be used in the solution of the optically active 2-methylpiperazine is preferably toluene, ethylbenzene, o-xylene, m-xylene, p-xylene, isopropanol, butanol, isobutanol, sec-butanol, tert-butanol, tetrahydrofuran, cyclopentyl methyl ether, diethyl ether, diisopropyl ether, or ethyl methyl ketone. More preferably, the solvent is toluene, ethylbenzene, o-xylene, m-xylene, p-xylene, tetrahydrofuran, or cyclopentyl methyl ether. As the solution of the optically active 2-methylpiperazine, the solution of the optically active 2-methylpiperazine containing water can also be used. The content of water in the solution is preferably 50 times or less by weight of the optically active 2-methylpiperazine. Further, the solution of the optically active 2-methylpiperazine may contain an alkali salt of carboxylic acid and/or an inorganic alkali or inorganic salt.

As a raw material, a solution of an optically active 2-methylpiperazine obtained by a method disclosed, for example, in JP 2004-161749 A can be used, in which method, 2-methylpiperazine in the form of a racemate is optically resolved with an optically active tartaric acid, and the resulting diastereomeric salt of an optically active 2-methylpiperazine and the optically active tartaric acid is decomposed with calcium hydroxide in a water solvent, to obtain the solution containing an optically active 2-methylpiperazine. Alternatively, aggregates of the optically active 2-methylpiperazine isolated by distillation can also be used as a raw material.

In the method of producing an optically active 2-methylpiperazine, a solvent is added to the solution of the optically active 2-methylpiperazine to carry out solvent replacement, and then crystals are formed from the resulting solvent-replaced solution. In particular, when the raw material is a solution of the optically active 2-methylpiperazine containing water, it is preferred that a solvent azeotropic with water be added to the solution, and after carrying out the solvent replacement to remove water, crystallization is occurred from the resulting solution, thereby separating the optically active 2-methylpiperazine as crystals. At this time, to improve production efficiency, it is preferred to concentrate the solution until the concentration of the optically active 2-methylpiperazine reaches 25% by weight or more to remove water by evaporation in advance, followed by adding a solvent azeotropic with water so that the solvent replacement can be carried out more efficiency.

It is preferred that a solvent azeotropic with water be used in the solvent replacement. Examples of the solvent azeotropic with water which can be used include: aromatic hydrocarbons such as benzene, toluene, ethylbenzene, xylene, styrene, chlorobenzene, and naphthalene; aliphatic hydrocarbons such as pentane, hexane, heptane, octane, nonane, decane, and dodecane; halogen-containing solvents such as carbon tetrachloride, chloroform, and 1,2-dichloroethane; alcohols such as, ethanol, propanol, isopropanol, butanol, isobutanol, sec-butanol, tert-butanol, pentanol, 2-pentanol, hexanol, heptanol, and octanol; aliphatic esters such as allyl acetate, isobutyl acetate, isopropyl acetate, isopentyl acetate, ethyl acetate, vinyl acetate, phenyl acetate, butyl acetate, propyl acetate, benzyl acetate, methyl acetate, isobutyl formate, butyl formate, methyl propionate, ethyl propionate, methyl butyrate, ethyl butyrate, propyl butyrate, isopropyl butyrate, butyl butyrate, isobutyl butyrate, pentyl butyrate, isopentyl butyrate, ethyl isobutyrate, methyl isovalerate, and ethyl isovalerate; aromatic esters such as methyl benzoate and ethyl benzoate; ethers such as tetrahydrofuran, cyclopentyl methyl ether, diethyl ether, diisopropyl ether, dibutyl ether, anisole, and diphenyl ether; ketones such as acetyl acetone, ethyl methyl ketone, cyclopentanone, cyclohexanone, 3-heptanone, 4-heptanone, 2-pentanone, and 3-pentanone and the like.

The solvent azeotropic with water preferably used is more preferably a water-insoluble organic solvent, and still more preferably, toluene or cyclopentyl methyl ether. The water-insoluble organic solvent as used herein refers to an organic solvent having a solubility in water of 10% or less, and preferably, 2% or less.

When a water-insoluble organic solvent is used as the solvent azeotropic with water preferably used, the distilled liquid will be separated into two layers of an aqueous layer and a water-insoluble organic solvent layer by using a Dean-Stark apparatus. Therefore, it is possible to remove only the aqueous layer out of the system and reuse the water-insoluble organic solvent layer, and thus, it is preferred in terms of economic efficiency.

When the solvent replacement is carried out, the amount to be used of the solvent azeotropic with water is preferably 20 times or less relative by weight of the optically active 2-methylpiperazine. When the amount used of the solvent azeotropic with water is 20 times or less relative by weight of the optically active 2-methylpiperazine, the production efficiency of the optically active 2-methylpiperazine tends to improve.

The solvent replacement is preferably carried out by a method in which a solvent used for the solvent replacement is added to the solution of the optically active 2-methylpiperazine, followed by concentration, and then the operation of further adding the solvent used for the solvent replacement and concentrating the resultant is repeated, to achieve the replacement of solvent; or a method in which a Dean-Stark apparatus is used to replace the solvent. The method using the Dean-Stark apparatus is more preferred because it reduces the production cost. When a water-insoluble organic solvent azeotropic with water is used, since the distillate obtained by concentrating and azeotropically dehydrating the solution is separated into two liquid layers, dehydration can be carried out easily, by repeating the operation of removing the aqueous layer out of the system while reintroducing the water-insoluble organic solvent back into the concentrated solution, until there is no aqueous layer left to be distilled. If the solution is concentrated excessively during the azeotropic dehydration, the optically active 2-methylpiperazine is gradually distilled out, resulting in a decrease in the yield. Therefore, it is preferred that the concentration of the optically active 2-methylpiperazine in the concentrated solution during the azeotropic dehydration be maintained at 10 to 70% by weight.

The pressure in the reaction system during the solvent replacement is preferably adjusted within the range of from normal pressure to 50 Torr, and more preferably from normal pressure to 100 Torr. The temperature in the reaction system during the solvent replacement is preferably 40 to 110° C., and more preferably 50 to 100° C.

The water content in the solution of the optically active 2-methylpiperazine in which water has been removed out of the system and replaced with a solvent azeotropic with water, is preferably 2% by weight or less, and more preferably 1% by weight or less. The lower the water content, the more preferred, because the amount of the optically active 2-methylpiperazine lost in the crystallization filtrate during the crystallization process can be reduced, thereby improving the yield.

It is preferred that the solution of the optically active 2-methylpiperazine in which water has been removed be concentrated so that the concentration of the 2-methylpiperazine is adjusted within the range of 30 to 60%.

When the solution of the optically active 2-methylpiperazine contains an alkali salt of carboxylic acid and/or an inorganic alkali or inorganic salt, the salt(s) is/are precipitated in the azeotropically dehydrated and solvent-replaced solution, and thus, the salt(s) can be removed out of the system by carrying out solid-liquid separation.

After adding a solvent to the solution of the optically active 2-methylpiperazine to carry out the solvent replacement, crystals of the optically active 2-methylpiperazine are obtained by crystallization. The crystallization may be carried out, for example, by a cooling crystallization process, an evaporation crystallization process, an anti solvent crystallization (drowning-out precipitation) process, a pressure crystallization process, or a reaction crystallization process. Preferred is a cooling crystallization process, an evaporation crystallization process, or an antisolvent crystallization process, and more preferred is a cooling crystallization process.

It is preferred that the solvent azeotropic with water and the solvent used in the crystallization be the same solvent.

It is more preferred that the solvent added to the solution of the optically active 2-methylpiperazine be a solvent azeotropic with water, and that the solvent azeotropic with water and the solvent used in the crystallization be the same solvent.

Examples of the solvent preferably used in the crystallization include: aromatic hydrocarbons such as benzene, toluene, ethylbenzene, o-xylene, m-xylene, p-xylene, styrene, chlorobenzene, and naphthalene; aliphatic hydrocarbons such as pentane, hexane, heptane, octane, nonane, decane, and dodecane; halogen-containing solvents such as carbon tetrachloride, dichloromethane, chloroform, and 1,2-dichloroethane; alcohols such as methanol, ethanol, propanol, isopropanol, butanol, isobutanol, sec-butanol, tert-butanol, pentanol, 2-pentanol, hexanol, heptanol, and octanol; aliphatic esters such as allyl acetate, isobutyl acetate, isopropyl acetate, isopentyl acetate, ethyl acetate, vinyl acetate, phenyl acetate, butyl acetate, propyl acetate, benzyl acetate, methyl acetate, isobutyl formate, butyl formate, methyl propionate, ethyl propionate, methyl butyrate, ethyl butyrate, propyl butyrate, isopropyl butyrate, butyl butyrate, isobutyl butyrate, pentyl butyrate, isopentyl butyrate, ethyl isobutyrate, methyl isovalerate, and ethyl isovalerate; aromatic esters such as methyl benzoate, and ethyl benzoate; ethers such as tetrahydrofuran, cyclopentyl methyl ether, diethyl ether, diisopropyl ether, dibutyl ether, anisole, and diphenyl ether; ketones such as acetone, acetyl acetone, ethyl methyl ketone, cyclopentanone, cyclohexanone, 3-heptanone, 4-heptanone, 2-pentanone, and 3-pentanone; nitriles such as acetonitrile and the like. The solvent to be used in the crystallization is preferably toluene, ethylbenzene, o-xylene, m-xylene, p-xylene, isopropanol, butanol, isobutanol, sec-butanol, tert-butanol, tetrahydrofuran, cyclopentyl methyl ether, diethyl ether, diisopropyl ether, or ethyl methyl ketone. More preferably, the solvent is toluene, ethylbenzene, o-xylene, m-xylene, p-xylene, tetrahydrofuran, or cyclopentyl methyl ether.

The solvent to be used in the crystallization is preferably one in which the solubility of the optically active 2-methylpiperazine at the temperature at which the optically active 2-methylpiperazine precipitated in the crystallization process is separated, is 40% by weight or less; and more preferably 30% by weight or less, from the viewpoint of the production efficiency.

The optically active 2-methylpiperazine is crystallized from the solvent-replaced solution of the optically active 2-methylpiperazine. The optically active 2-methylpiperazine by crystallization is preferably obtained crystals of the optically active 2-methylpiperazine by solid-liquid separation. By concentrating the filtrate to adjust the concentration of the optically active 2-methylpiperazine, and then carrying out the crystallization again, as required, it is possible to obtain an additional amount of crystals of the optically active 2-methylpiperazine. A high yield of the optically active 2-methylpiperazine can be achieved, by totaling the amount of the optically active 2-methylpiperazine obtained in the first crystallization with that obtained in the subsequent crystallization(s). The recycling of the filtrate as a solvent is also possible, and the filtrate can be reused as the solvent when carrying out the crystallization of the optically active 2-methylpiperazine again.

The temperature at which seed crystals of the optically active 2-methylpiperazine are added varies depending on the concentration of the optically active 2-methylpiperazine. However, the temperature is usually lower than the melting point of the optically active 2-methylpiperazine, and is 60° C. or less, more preferably from 15 to 55° C. The slurry solution in which the crystals of the optically active 2-methylpiperazine are precipitated is further cooled. The cooling temperature of the solution before being subjected to solid-liquid separation is preferably −20 to 10° C., and more preferably −15 to 5° C. To obtain the crystals of the optically active 2-methylpiperazine at a stable yield, it is necessary that the solution be allowed to age for a sufficient period of time, at the temperature at which the solution is cooled before being subjected to the solid-liquid separation. The aging time is usually 0.5 to 24 hours, and more preferably 1 to 20 hours. By subjecting the resulting slurry solution to solid-liquid separation using a centrifugal draining machine or a pressure filter, and then drying, the crystals of the optically active 2-methylpiperazine can be obtained.

By obtaining the optically active 2-methylpiperazine as crystals, as described above, it is possible to obtain an optically active 2-methylpiperazine having a higher purity than the optically active 2-methylpiperazine contained in the raw material. When an optical isomer of the 2-methylpiperazine is contained, it has been difficult to remove it by distillation. However, the optical isomer of the 2-methylpiperazine can also be removed. Further, since the optically active 2-methylpiperazine isolated by distillation is solidified in the form of aggregates, handling of the resulting 2-methylpiperazine has been troublesome. The crystals of the optically active 2-methylpiperazine obtained have fluidity and, thus, they can be easily handled when they are weighed, dissolved or transferred.

The method of producing an optically active 2-methylpiperazine using toluene or cyclopentyl methyl ether will now be described, as an example.

First, the solution of the optically active 2-methylpiperazine as a raw material is charged. The solution is concentrated until the concentration of the optically active 2-methylpiperazine reaches 25% by weight or more. When the solution already has a concentration of the optically active 2-methylpiperazine of 25% by weight or more, this operation can be omitted. Then toluene or cyclopentyl methyl ether is added to the resultant, and solvent replacement is carried out using a Dean-Stark apparatus. The pressure in the reaction system during the solvent replacement is preferably adjusted within the range of from normal pressure to 50 Torr, and more preferably, normal pressure to 100 Torr. The temperature in the reaction system during the solvent replacement is preferably 40 to 110° C., and more preferably 50 to 100° C. Only the aqueous layer, of the distilled liquid, is removed out of the system, and azeotropic distillation is continued until there is no water left to be distilled. When an alkali salt of carboxylic acid and/or an inorganic alkali or inorganic salt is/are precipitated in the resulting dehydrated and solvent-replaced solution of the optically active 2-methylpiperazine, the solution is cooled, and then subjected to solid-liquid separation to remove the precipitated alkali salt of carboxylic acid and/or inorganic alkali or inorganic salt out of the system. The dehydrated solution of the optically active 2-methylpiperazine in toluene or in cyclopentyl methyl ether is concentrated to adjust the concentration of the 2-methylpiperazine to 30 to 60%.

The slurry solution in which the crystals of the optically active 2-methylpiperazine are precipitated is further cooled. To obtain the crystals of the optically active 2-methylpiperazine at a stable yield, it is necessary that the solution be allowed to age for a sufficient period of time, at the temperature at which the solution is cooled before being subjected to the solid-liquid separation. By subjecting the resulting slurry solution to solid-liquid separation using a centrifugal draining machine or a pressure filter and then drying, the crystals of the optically active 2-methylpiperazine can be obtained.

EXAMPLES

Our methods will now be described in further detail, by way of Examples. The description will be given below, using an optically active 2-methylpiperazine an example.
Measurement of Chemical Purity of Optically Active 2-Methylpiperazine The measurement of the chemical purity of the optically active 2-methylpiperazine was carried out by gas chromatography (GC). The conditions for analysis are as follows.
  Type of apparatus: Shimadzu GC-17A
  Column: InertCap-1, 0.25 mm diameter×60 m
  Helium flow rate: 50 ml/min.
  Column temperature: 70° C. (10 min.)→(+20° C./min.) →270° C. (10 min.)
  Inlet temperature: 230° C.
  Detector temperature: 230° C.
  Detector: FID
  Injection volume: 1.0 µl
  Retention time: 2-methylpiperazine, 10.2 min.
Measurement of Optical Purity of Optically Active 2-Methylpiperazine The optical purity of the optically active 2-methylpiperazine in the resulting crystals was measured by liquid chromatography, and calculated from the peak area ratio of the R-form and S-form. When the S-form is selectively formed, the optical purity is calculated according to the following formula:

Optical purity (% e.e.)=(peak area value of S-form−peak area value of R-form)/(peak area value of S-form+peak area value of R-form)×100.

The conditions for analysis are as follows.
Type of apparatus: Shimadzu LC-10Vp
Column: Mightysil RP18GP, 4.6 mm×15 cm (Kanto Chemical Co., Inc.)
Mobile phase: 0.03% ammonia water (prepared to a pH of 4.7 with acetic acid)/acetonitrile=67/33 (v/v)
Flow rate: 1.0 ml/min.
Temperature: 40° C.
Detector: UV (243 nm)
Injection volume: sample preparation solution 5.0 µl Preparation of sample: A quantity of about 40 mg of the crystals of the optically active 2-methylpiperazine was weighed and placed in a 50 ml measuring flask, and diluted with acetonitrile up to the marked line of the measuring flask. A quantity of 0.1 ml of the resultant was collected and placed in a 2 ml sample bottle, and 0.5 ml of a 0.8% solution of O,O'-p-ditoluoyl-L-tartaric anhydride in acetonitrile was added thereto, followed by allowing the resulting solution to stand in a warm bath at 50° C. for 1 hour. Finally, 0.1 ml of 0.05% phosphoric acid water was added to the solution, followed by allowing the resultant to stand at room temperature for 10 minutes.

Reference Example 1

To a 2 L four-necked flask equipped with a thermometer, a vacuum stirrer, and a condenser tube, 270 g (1.8 mol) of L-tartaric acid, 108 g (1.8 mol) of acetic acid, and 270 g of water were added, and the components were allowed to completely dissolve. To the resultant, 300 g (3.0 mol) of (±)-2-methylpiperazine and 300 g of water were then added, and the resulting reaction solution was heated to 85° C. or more to completely dissolve the 2-methylpiperazine. The resulting solution was then cooled to 68 to 74° C., and a diastereomeric salt of (R)-2-methylpiperazine and L-tartaric acid was added to precipitate crystals, and the resultant was allowed to age at that temperature for 1 hour. Subsequently, the resulting solution was cooled to 12 to 18° C. over 5 hours, and the precipitated crystals were filtered, to obtain 440 g of diastereomeric salt in a wet state, having a liquid content of 22.7 wt %, and an optical purity of 92.3% e.e. The yield of the R-form in the obtained salt with respect to the amount of the R-form contained in the charged (±)-2-methylpiperazine was 88%.

Next, 644 g of water was charged into a 2 L four-necked flask, and 440 g of the resulting crystals (the amount of pure (R)-2-methylpiperazine=132 g) was added thereto. Further, 162 g (2.2 mol) of hydroxide calcium was added, and the resultant was then heated to 80° C., and allowed to age at that temperature for 5 hours. The resultant was then cooled to 25° C. over 2 hours, and the precipitated crystals were filtered and separated, to remove 586 g of wet crystals (mainly, L-calcium tartrate). A quantity of 660 g of the resulting filtrate was collected, and 130 g of (R)-2-methylpiperazine liberated from L-tartaric acid was present in the filtrate.

Example 1

To a 1 L four-necked flask equipped with a thermometer, a vacuum stirrer and a condenser tube, 330 g of the filtrate (containing 65 g of (R)-2-methylpiperazine) obtained in Reference Example 1 was charged. The resultant was concentrated under reduced pressure, and water was removed by distillation until the concentration of the (R)-2-methylpiperazine reaches 30%. To the concentrate, 356 g of toluene was added. The resulting mixed solution was heated, and water was azeotropically distilled with toluene at 84 to 87° C. under normal pressure, to remove water. Then 212 g of toluene was removed by distillation under reduced pressure. The resulting concentrate was cooled to 47° C., and 0.01 g of (R)-2-methylpiperazine was added as seed crystals to precipitate crystals, and the resultant was allowed to age at 47° C. for 1 hour. Then the resultant was cooled to 0 to 5° C. over 5 hours, and allowed to age at 0 to 6° C. for 2 hours. The precipitated crystals were collected by filtering under reduced pressure, and vacuum dried to obtain 45 g of (R)-2-methylpiperazine in the form of crystals. The thus obtained crystals of the (R)-2-methylpiperazine had a chemical purity of 100%, and an optical purity of 99.5% e.e. The yield of the crystals of the (R)-2-methylpiperazine with respect to the amount of the R-form contained in the charged filtrate was 69%.

FIG. 1 illustrates a process flow chart showing the steps carried out in Reference Example 1 through Example 1. There were 6 steps from the first crystallization ("referred to as Crystallization 1") through the last crystallization ("referred to as crystallization") in total. The process flow shown in FIG. 1 has less number of steps as compared to the process flow of Comparative Example 2, and it was possible to obtain an optically active 2-methylpiperazine having a good handleability and favorable properties, with the process flow shown in FIG. 1.

Example 2

To a 1 L four-necked flask equipped with a thermometer, a vacuum stirrer and a condenser tube, 330 g of the filtrate (containing 65 g of (R)-2-methylpiperazine) obtained in Reference Example 1 was charged. The resultant was concentrated under reduced pressure, and water was removed by distillation until the concentration of the (R)-2-methylpiperazine reaches 30%. To the concentrate, 356 g of cyclopentyl methyl ether was added. The resulting mixed solution was heated, and water was azeotropically distilled with cyclopentyl methyl ether at 84 to 87° C. under normal pressure, to remove water. Then 205 g of cyclopentyl methyl ether was removed by distillation under reduced pressure. The resulting concentrate was cooled to 47° C., and 0.01 g of (R)-2-methylpiperazine was added as seed crystals to precipitate crystals, and the resultant was allowed to age at 47° C. for 1 hour. Then the resultant was cooled to 0 to 5° C. over 5 hours, and allowed to age at 0 to 6° C. for 2 hours. The precipitated crystals were collected by filtering under reduced pressure, and vacuum dried to obtain 44 g of (R)-2-methylpiperazine in the form of crystals. The thus obtained crystals of the (R)-2-methylpiperazine had a chemical purity of 100%, and an optical purity of 99.6% e.e. The yield of the crystals of the (R)-2-methylpiperazine with respect to the amount of the R-form contained in the charged filtrate was 68%.

Example 3

To a 1 L four-necked flask equipped with thermometer, a vacuum stirrer, and a Dean-Stark apparatus, 300.0 g of 33% aqueous solution of (S)-2-methylpiperazine ((S)-2-methylpiperazine 100.0 g; quality: chemical purity: 99.9%; optical purity: 80.0% e.e.) was charged. Then 586.0 g of toluene (5.86 times the weight of the (S)-2-methylpiperazine) was added to the resultant, followed by stirring. The resulting solution was heated, and water was azeotropically distilled with toluene at 84 to 87° C. under normal pressure, to remove water alone. Then 286 g of toluene was removed by distillation under reduced pressure. The resulting concentrate was cooled to 43 to 50° C., and 0.01 g of (S)-2-methylpiperazine was added as seed crystals to precipitate crystals, and the resultant was allowed to age at 43 to 50° C. for 1 hour. Then the resultant was cooled to 0 to 5° C. over 2 hours, and allowed to age at 0 to 5° C. for 2 hours. The precipitated crystals were collected by filtering under reduced pressure, and vacuum dried to obtain 66.8 g of (S)-2-methylpiperazine in the form of crystals (yield: 67%). The thus obtained crystals of the (S)-2-methylpiperazine had a chemical purity of 100%, and an optical purity of 99.4% e.e.

Comparative Example 1

To a 1 L four-necked flask equipped with a thermometer, a condenser and an agitator, 300.0 g of 33% aqueous solution of (S)-2-methylpiperazine ((S)-2-methylpiperazine 100.0 g (1.0 mol); quality: chemical purity: 99.9%, optical purity: 80.0% e.e.) was charged, and the resultant was concentrated and distilled to obtain 13.3 g (0.13 mol) of (S)-2-methylpiperazine (yield: 13%). The resulting (S)-2-methylpiperazine was solidified and in the form of aggregates. The (S)-2-methylpiperazine in the form of aggregates was completely dissolved, and then sampling was carried out to perform the analysis and the evaluation of the (S)-2-methylpiperazine. The resulting (S)-2-methylpiperazine had a chemical purity of 99.9% and an optical purity of 80.0% e.e, which were the same as those of the (S)-2-methylpiperazine contained in the charged solution, but about 10% of water was contained.

Example 4

To a 1 L four-necked flask equipped with a thermometer, a vacuum stirrer and a condenser tube, 500.0 g of aqueous solution of 30% (S)-2-methylpiperazine ((S)-2-methylpiperazine 150.0 g; quality: chemical purity: 99.9%, optical purity: 99.7% e.e.) was charged. Then 525.1 g (3.5 times the weight of the (S)-2-methylpiperazine) of toluene was added to the resultant, followed by stirring. Then the resulting solution was concentrated under a reduced pressure of 147 mmHg at 48° C., to remove 501.3 g of liquid by distillation. The distilled liquid was separated into two liquid layers of a toluene layer and an aqueous layer, and 56.0 g of the aqueous layer was removed, and 445.3 g of the toluene layer was mixed with the concentrate.

The resulting mixed solution was then concentrated under a reduced pressure of from 136 to 138 mmHg at 48° C., to remove 535.0 g of liquid by distillation. The distilled liquid was separated into two liquid layers of a toluene layer and an aqueous layer, and 61.9 g of the aqueous layer was removed, and 473.1 g of the toluene layer was mixed with the concentrate.

Then 100 g of toluene (0.7 times the weight of the (S)-2-methylpiperazine) was added to the resultant, followed by stirring. The resulting solution was concentrated under a reduced pressure of 137 mmHg at 47° C., to remove 565.8 g of liquid by distillation. The distilled liquid was separated into two liquid layers of a toluene layer and an aqueous layer, and 64.8 g of the aqueous layer was removed, and 501.0 g of the toluene layer was mixed with the concentrate.

The resulting mixed solution was then concentrated under a reduced pressure of 138 mmHg at 48° C., to remove 492.7 g of liquid by distillation. The distilled liquid was separated into two liquid layers of a toluene layer and an aqueous layer, and 52.5 g of the aqueous layer was removed, and 440.2 g of the toluene layer was mixed with the concentrate.

Then 100 g of toluene (0.7 times the weight of the (S)-2-methylpiperazine) was added to the resultant, followed by stirring. The resulting solution was concentrated under a reduced pressure of 138 mmHg at 48° C., to remove 469.7 g of liquid by distillation. The distilled liquid was separated into two liquid layers of a toluene layer and an aqueous layer, and 54.4 g of the aqueous layer was removed, and 415.3 g of the toluene layer was mixed with the concentrate.

The resulting mixed solution was then concentrated under a reduced pressure of from 147 to 149 mmHg at 50 to 51° C., to remove 456.7 g of liquid by distillation. The distilled liquid was separated into two liquid layers of a toluene layer and an aqueous layer, and 57.2 g of the aqueous layer was removed, and 399.5 g of the toluene layer was mixed with the concentrate.

Then 100 g of toluene (0.7 times the weight of the (S)-2-methylpiperazine) was added to the resultant, followed by stirring. The resulting solution was concentrated under a reduced pressure of from 147 to 153 mmHg at 56° C., to remove 98.4 g of liquid by distillation. The distilled liquid was separated into two liquid layers of a toluene layer and an aqueous layer, and 11.3 g of the aqueous layer was removed, and the weight of the toluene layer was 87.1 g.

The concentrate was allowed to cool to 10° C. over 5 hours. During the cooling, crystals precipitated at 30° C. Subsequently, the resultant was allowed to age at 10 to 15° C. for 1 hour, and the precipitated crystals were collected by filtering under reduced pressure, and vacuum dried to obtain 87.7 g of 2-methylpiperazine in the form of crystals (yield: 58.3%). The thus obtained crystals of the (S)-2-methylpiperazine had a chemical purity of 100%, and an optical purity of 100% e.e.

The filtrate obtained by the filtration was concentrated under a reduced pressure of from 147 to 153 mmHg at 56° C., to remove 611.7 g of liquid by distillation. The concentrate was allowed to cool to 5° C. over 5 hours. During the cooling, crystals precipitated at 45° C. Subsequently, the resultant was allowed to age at 5 to 10° C. for 1 hour, and the precipitated crystals were collected by filtering under reduced pressure, and vacuum dried to obtain 28.2 g of 2-methylpiperazine in the form of crystals (yield: 18.8%). The thus obtained crystals of the (S)-2-methylpiperazine had a chemical purity of 100%, and an optical purity of 100% e.e. The total amount of (S)-2-methylpiperazine collected by the crystallization carried out twice amounted to 115.9 g, and the total yield was 77.3%.

Comparative Example 2

A quantity of 15.0 g (0.15 mol) of (±)-2-methylpiperazine, 69.8 g (0.42 mol) of (R)-2-phenoxypropionic acid, and 250 ml of 2-propanol were mixed, and the resultant was heated to reflux to dissolve the contents. After dissolving the contents, the solution was cooled to 25° C. overnight. Then precipitated crystals were separated and dried to obtain 48.0 g of crude diastereomeric salt. $[\alpha]_D$: +21.2° (C=1.0 methanol).

The thus obtained crude diastereomeric salt was recrystallized from 2-propanol twice ("referred to as Crystallization 2 and Crystallization 3 in FIG. 2), to obtain 41.3 g of purified diastereomeric salt of (R)-2-methylpiperazine III ((R)-2-phenoxypropionic acid). $[\alpha]_D$: +23.0° (C=1.0 methanol), melting point: 149° C.

A quantity of 41.3 g (69 mmol) of the purified diastereomeric salt, 140 ml of dichloromethane, 25.0 g (0.24 mol) of 35% hydrochloric acid, and 25 ml of distilled water were mixed to decompose the salt. When the solids were dissolved, the resulting solution was allowed to stand, followed by liquid separation. The resulting aqueous layer was concentrated to dryness to obtain 11.7 g of (R)-2-methylpiperazine dihydrochloride. $[\alpha]_D$: +5.33° (C=1.0 formic acid)

A quantity of 10.0 g (58 mmol) of the (R)-2-methylpiperazine dihydrochloride and 23.2 g (0.12 mol) of a solution of 28% sodium methoxide in methanol were mixed and stirred at 25° C. for 1 hour to carry out liberation. After filtering the insolubles, the solvent was removed by evaporation. To the residue, 30 ml of cyclohexane was added, and the resultant was heated to reflux. Then the solution was subjected to hot filtration to remove insolubles, followed by cooling to 20° C. Then precipitated crystals were separated and dried to obtain 4.5 g of (R)-2-methylpiperazine (yield: 60.0%). $[\alpha]_D$: −20.3° (C=1.0 t-butyl methyl ether). The crystals had an optical purity of 99.6% e.e., and a melting point of 90° C.

Figure 2:
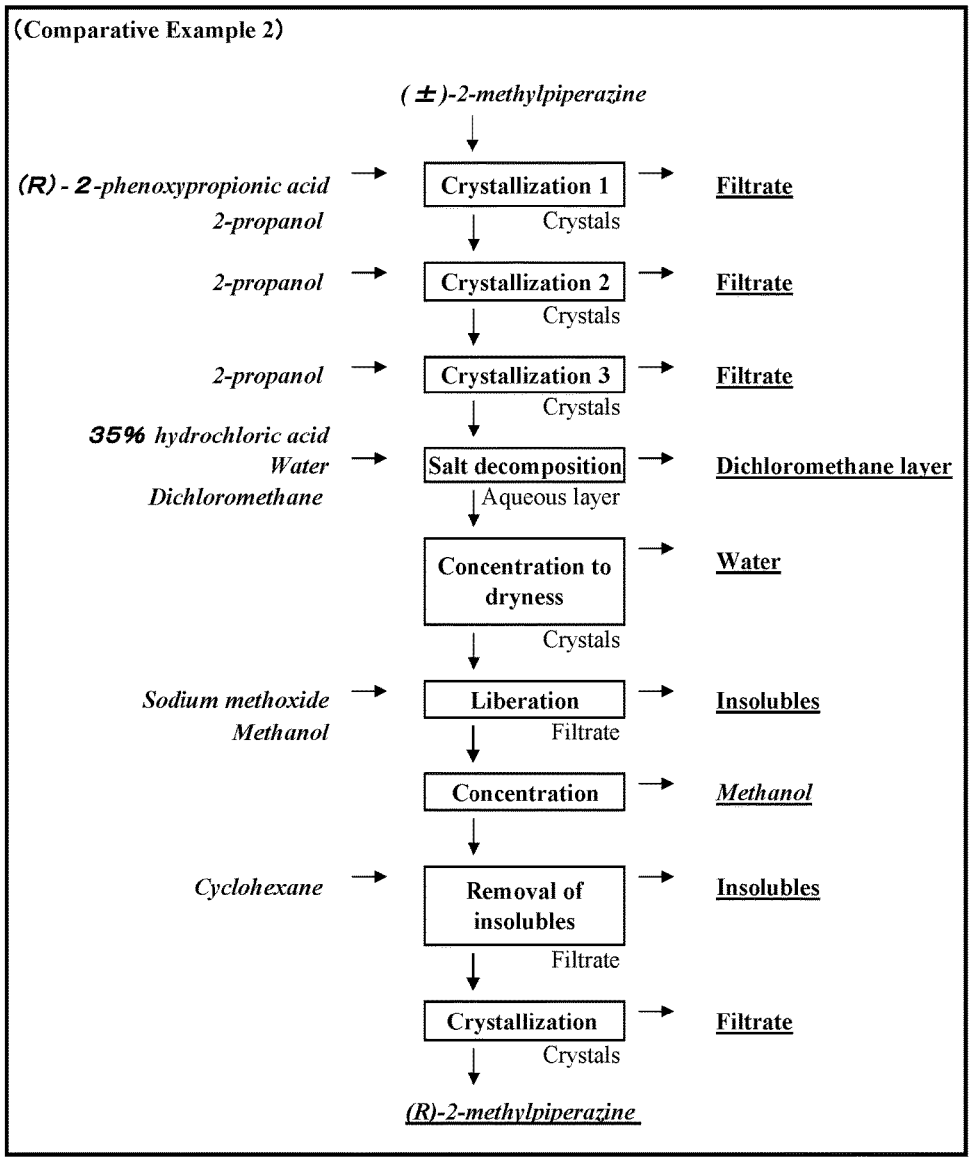
FIG. 2 is a process flow chart illustrating the steps carried out in Comparative Example 2.

FIG. 2 illustrates a process flow chart showing the steps carried out in Comparative Example 2. The operation carried out in Comparative Example 2 was complicated, requiring a number of steps.

INDUSTRIAL APPLICABILITY

The method of producing an optically active 2-methylpiperazine is an industrially advantageous method because it has a short production process. Further, since the method of producing an optically active 2-methylpiperazine allows the optically active 2-methylpiperazine to be purified during the crystallization process, it is possible to obtain an optically active 2-methylpiperazine having a high quality.

The optically active 2-methylpiperazine produced by the method of producing an optically active 2-methylpiperazine is useful as a raw material for pharmaceuticals.

The invention claimed is:

1. A method of producing an optically active 2-methylpiperazine comprising:
    adding a toluene or cyclopentyl methyl ether to a solution of the optically active 2-methylpiperazine to carry out solvent replacement,
    adding optically active 2-methylpiperazine as a seed crystal, and
    then obtaining crystals of the optically active 2-methylpiperazine by crystallization.

2. The method according to claim 1, wherein the solvent to be added to the solution of the optically active 2-methylpiperazine to carry out the solvent replacement, and a solvent used in the crystallization are the same solvent.

* * * * *